(12) United States Patent
Krueger et al.

(10) Patent No.: US 8,389,215 B2
(45) Date of Patent: Mar. 5, 2013

(54) NON-INVASIVE RECOVERY OF RNA AND ANALYSIS OF GENE EXPRESSION IN SKIN

(75) Inventors: Gerald Krueger, Salt Lake City, UT (US); Nicholas Benson, San Diego, CA (US)

(73) Assignee: University of Utah Research Foundation, Salt Lake City, UT (US)

( * ) Notice: Subject to any disclaimer, the term of this patent is extended or adjusted under 35 U.S.C. 154(b) by 230 days.

(21) Appl. No.: 12/452,872

(22) PCT Filed: Jul. 28, 2008

(86) PCT No.: PCT/US2008/009151
§ 371 (c)(1),
(2), (4) Date: Jan. 25, 2010

(87) PCT Pub. No.: WO2009/014766
PCT Pub. Date: Jan. 29, 2009

(65) Prior Publication Data
US 2010/0129801 A1    May 27, 2010

Related U.S. Application Data

(60) Provisional application No. 60/952,214, filed on Jul. 26, 2007.

(51) Int. Cl.
*C12Q 1/68* (2006.01)
*C07H 21/00* (2006.01)
(52) U.S. Cl. .......... 435/6.1; 536/22.1; 536/25.4
(58) Field of Classification Search .......... 435/6.1; 536/22.1, 23.1, 24.3, 25.4
See application file for complete search history.

(56) References Cited

U.S. PATENT DOCUMENTS

| | | | |
|---|---|---|---|
| 4,105,715 A * | 8/1978 | Gleave | 525/276 |
| 4,842,610 A * | 6/1989 | Gordon et al. | 8/160 |
| 5,254,132 A * | 10/1993 | Barley et al. | 606/214 |
| 5,620,852 A | 4/1997 | Lin et al. | |
| 5,990,302 A | 11/1999 | Kuroita et al. | |
| 6,566,127 B1 * | 5/2003 | Pavco et al. | 435/325 |
| 7,183,057 B2 * | 2/2007 | Benson | 435/6.14 |
| 7,267,950 B2 | 9/2007 | Belly et al. | |
| 7,615,349 B2 * | 11/2009 | Riker et al. | 435/6.12 |
| 7,989,165 B2 * | 8/2011 | Benson | 435/6.17 |
| 2002/0197633 A1 * | 12/2002 | Jones et al. | 435/6 |
| 2003/0096749 A1 * | 5/2003 | Kuestner et al. | 514/12 |
| 2003/0225345 A1 * | 12/2003 | Slavtcheff et al. | 600/572 |
| 2004/0170673 A1 * | 9/2004 | Koch et al. | 424/449 |
| 2005/0221334 A1 * | 10/2005 | Benson | 435/6 |
| 2006/0078894 A1 * | 4/2006 | Winkler et al. | 435/6 |
| 2006/0078902 A1 * | 4/2006 | Bunting et al. | 435/6 |
| 2006/0105372 A1 * | 5/2006 | Bair et al. | 435/6 |

FOREIGN PATENT DOCUMENTS

WO    WO-02-15800 A1    2/2002

OTHER PUBLICATIONS

Chirgwin et al. Isolation of biologically active ribonucleic acid from sources enriched in ribonuclease. Biochemistry 18 (24) : 5294 (1979).*

Chomczynski et al., Single-step method of RNA isolation by acid guanidinium thiocyanate-phenol-chloroform extraction. Analytical Biochemistry 162(1) : 156 (1987).*

Chomczynski et al., A reagent for the single-step simultaneous isolation of RNA, DNA and proteins from cell and tissue samples. Biotechniques 15(3):532 (1993).*

Hansen et al. J. of Investigative Dermatology 121(1) : Meeting Abstract No. 1200 (Jul. 2003).*

* cited by examiner

*Primary Examiner* — Ethan C Whisenant
(74) *Attorney, Agent, or Firm* — Ballard Spahr LLP

(57) ABSTRACT

A liquid is placed on an area of skin in which an RNA sample is to be extracted. The liquid is configured to harden which allows for the hardened material to be peeled off. In some implementations, a substrate is attached to the liquid before it hardens to facilitate removal of the skin sample.

17 Claims, 2 Drawing Sheets

NON-INVASIVE RECOVERY OF RNA AND ANALYSIS OF GENE EXPRESSION IN SKIN

CROSS-REFERENCE TO RELATED APPLICATIONS

The present application is a U.S. national phase filing under 35 U.S.C. 371 of International Patent Application No. PCT/US2008/009151, filed Jul. 28, 2008, which claims the benefit of U.S. Provisional Patent Application No. 60/952,214, filed Jul. 26, 2007, each of which are hereby incorporated by reference in their entirety.

TECHNICAL FIELD

The present invention relates to methods of noninvasively recovering RNA from skin. In one embodiment, the recovered RNA may be quantified and the relative level of particular genes assessed in order to predict a patient's response to a drug.

BACKGROUND

Human skin is a unique tissue and the human body's largest organ. The skin is composed of two layers; the epidermis is the outermost relatively thin layer; and the dermis is the inner relatively thick layer. The two layers are bound together by the basal lamina. The epidermis forms a barrier whose primary function is protective and it is also essential to life. It is composed of four general sub-layers; the stratum germinativum or basal layer (the most inner layer and whose cells abut the basallamina; the stratum spinosum, the stratum granulosum and the stratum corneum, the outermost layer). Each of these layers is derived from cells of the preceding layer, with new cells generated from the basal layer, which contains mitotically active keratinocytes and stem cells. The first three layers all serve to create the stratum corneum, which is the functional barrier for water retention, pathogen exclusion and protection from chemical and or physical elements in the environment. A normal healthy epidermis renews itself on average every 30 days.

The outer and essential stratum corneum is produced as the end product of an orchestrated suite of keratinocyte differentiation and differential gene expression, leading to terminal differentiation and cell death. The stratum corneum is therefore composed of enucleate, "dead" cells. If the process of differentiation of cells to produce the stratum corneum is perturbed, the consequences can be dramatic, resulting in any of a variety of diseases, many of which are fatal.

Key to the biology of the epidermis and the production of a healthy stratum corneum is differential gene expression, which precedes and directs keratinocyte differentiation. Because changes in gene expression precede or accompany changes in skin physiology, monitoring gene expression in the skin in health and disease is of particular medical interest. Changes in gene expression are conveniently measured as changes in messenger RNA (mRNA) levels or specific proteins within the cell.

Traditional methods for the recovery of nucleic acids (RNA and DNA) and proteins from the skin are invasive, i.e. the punch or shave biopsy. These sampling methods require the use of a scalpel or other sharp instrument (e.g. dermatome, curette) to recover a tissue specimen. These sampling methods invariably isolate epidermis as well as dermis, require local anesthesia, create bleeding wounds, produce scarring and in the case of biopsies greater than 3 mm, generally require sutures to close the skin. Biopsy sites represent direct access for pathogens to the body and thus are sites of potential internal and superficial (skin) infection to healthy individuals. People who are immunocompromised or diabetic and have impaired wound healing may be at higher risk for infections from biopsy procedures. However, the information gained from biopsy (e.g. diagnosis of disease, physiological data) typically outweighs the slight risk that biopsy presents. Nonetheless, any method that can produce similar information but avoids wounding and the risk of infection would be preferable to biopsy.

Before 1999 there were few alternatives to skin biopsy if the goal was to isolate a skin sample for molecular analysis, such as DNA or RNA analysis. Use of the polymerase chain reaction in quantification of interleukin 8 mRNA in minute epidermal samples utilized curettage (scraping) to isolate superficial skin samples for subsequent analysis by reverse transcription PCR analysis (RT-PCR) of IL-8 mRNA expression. However, scraping is highly dependant on the skill of the operator if bleeding is to be avoided and the method has never been used as a routine technique for skin sampling. Thus until 1999 there was no simple and non-invasive method of procuring a sample for the analysis of RNA expression in the skin.

In 1999 it was demonstrated that a well known method of superficial skin removal, tape stripping, could be used to recover RNA from the skin. It was shown that tape strip recovered RNA could be used to differentiate irritant from allergic contact dermatitis. Unfortunately, this method was not practical because it usually took more than 20 applications of fresh tape to recover a sample.

In 2004 it was demonstrated that the first four applications of tape were sufficient in most cases to obtain an RNA sample. The recovered RNA was capable of analysis by RT-PCR and DNA microarray technologies. The method has also been utilized to collect RNA for RT-PCR analysis of RNA from psoriatic lesions. Further work by researchers in this field demonstrated that recovery of RNA from the skin was (i) reproducibly variable; (ii) that recovery varied significantly at different anatomical locations on the same individual; and (iii) that recovery varied between individuals at similar anatomical locations.

The variability of RNA recovery by tape stripping resembles the variability in yield of stratum corneum by tape stripping and the variation in recovery of topically applied drugs. The source of this variation is believed to lie in the nature of the skin surface as skin is irregular, with natural crevasses, contours, and wrinkles all conspiring to create a rough and variable surface. Features such as hair follicles, sweat and sebaceous ducts also create "holes" in the stratum corneum that contribute to additional surface irregularity. It has been demonstrated that adhesive tape, with its limited ability to conform to microscopic structures cannot mold itself to surface irregularities and thus cannot remove a uniform layer of skin. Tape stripping of human stratum corneum yields cell layers that originate from various depths because of furrows in the skin. Repeated tape stripping does not immediately solve this problem.

An additional deficiency to the use of adhesive tape to recover skin samples (hence RNA) is the variability in adhesion to the skin encountered with different operators. It has been reported that differing applied pressures and methods of applying pressure result in different degrees of adhesion to the skin and consequentially differential removal of a sample. While some groups have mitigated this deficiency by applying a measured amount of force when applying tape in experimental situations, this added step would be an encumbrance in a clinical situation. These encumbrances are clearly revealed by the preponderance of published clinical trials employing tape stripping where method and applied pressure are uncontrolled variables.

The use of adhesive tape is further made inconvenient in a clinical and commercial setting by restrictions imposed by the physical dimensions of the tape itself. By necessity tape comes in a particular size; however, skin lesions come in a range of sizes and shapes. When faced with a tape of particular dimensions an operator must pay particular attention to applying the tape to the lesion alone and avoiding the surrounding non-lesional skin. This lesion-only application can never be sure of completely avoiding surrounding non-lesional skin and thus the potential for contamination of the lesional sample with non-lesional skin cannot be completely eliminated. While this size limitation could be partially overcome by supplying tape in a variety of sizes and shapes, this solution would lead to highly inefficient use of tape.

SUMMARY

The present invention discloses methods of isolating RNA molecules from skin.

In one aspect, the present invention provides a method for isolating RNA molecules from a skin sample by applying a liquid to the skin surface, applying a substrate to the liquid, allowing the liquid to harden, removing the substrate, removing the skin sample from the resulting solid phase of the liquid, and isolating RNA from said skin sample.

In another aspect, the present invention provides a method isolating RNA molecules from a skin sample by applying a liquid to a skin surface, allowing the liquid to harden, removing the liquid, removing the skin sample from the liquid, and isolating RNA from the skin sample.

In one embodiment, the liquid is a sutureless wound closing agent. In a particular embodiment, the sutureless wound closing agent is selected from the group consisting of Dermabond (Braun Surgical Gmbh, Melsungen, Germany), Histoacryl (Ethicon Inc., Johnson & Johnson, N.J.) and Indermil® (Covidean, Mansfield, Mass.)

In another embodiment, the substrate is selected from the group consisting of a glass slide, a spatula, a plastic film, cloth or plastic.

In another embodiment, the skin sample is collected from a location on a patient selected from the group consisting of the upper back, mastoid process, hand, foot and deltoid.

In another embodiment, the RNA is quantified from a variety of locations. In a particular embodiment, the locations include skin that is lesional and unaffected. In another particular embodiment, the lesional skin areas are due to a skin disorder. In a particular embodiment, the skin disorder is due to psoriasis and atopic dermatitis.

In a further embodiment, the RNA is further quantified. In a particular embodiment, it is quantified for the relative levels of transcripts for GAPDH, TNF-α, VEGF and K16. In another embodiment, such quantification is predictive of a patient's response to a drug. In a particular embodiment, such patient has psoriasis and the drug is enbrel.

In another embodiment, a kit is provided with materials necessary for isolating RNA molecules from a skin sample. In a particular embodiment, the kit includes a liquid, a substrate, a cell lysis buffer suitable of preserving RNA, and instructions for using the kit to isolate RNA molecules from a skin sample.

The details of one or more variations of the subject matter described herein are set forth in the accompanying drawings and the description below. Other features and advantages of the subject matter described herein will be apparent from the description and drawings, and from the claim.

DETAILED DESCRIPTION

Definitions

"Nucleic acid" and "oligonucleotide" have the meaning that is commonly-known in the art, and includes primers, probes, and oligomer fragments, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

"Fragment" is meant to refer to any subset of the referent protein or nucleic acid molecule.

"Hybridization" has the meaning that is commonly-known in the art, that is, the formation of a duplex structure by two single-stranded nucleic acids due to complementary base pairing. Hybridization can occur between exactly complementary nucleic acid strands or between nucleic acid strands that contain some regions of mismatch.

The term, "skin" has the meaning of a tissue including a sheet of cells that is several layers thick, organized above a basal lamina.

The term, "sample" means a skin sample derived from the skin of a subject. This can include sampling directly from the skin of a patient, as well as from an in-vitro culture of a patient's skin.

The term, "skin lesion" refers to any change in the color or texture of an area of skin. An area of skin with a lesion may be referred to as, "lesional."

Moreover, for the purpose of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from a natural source, can be produced using molecular biology techniques or can be produced by chemical synthesis.

DESCRIPTION OF THE DRAWINGS

The drawings below are for illustration purposes only. The drawings are not intended to limit the scope of the applicant's teachings in any way.

METHODS OF COLLECTING RNA FROM A SKIN SAMPLE

Figure 1:
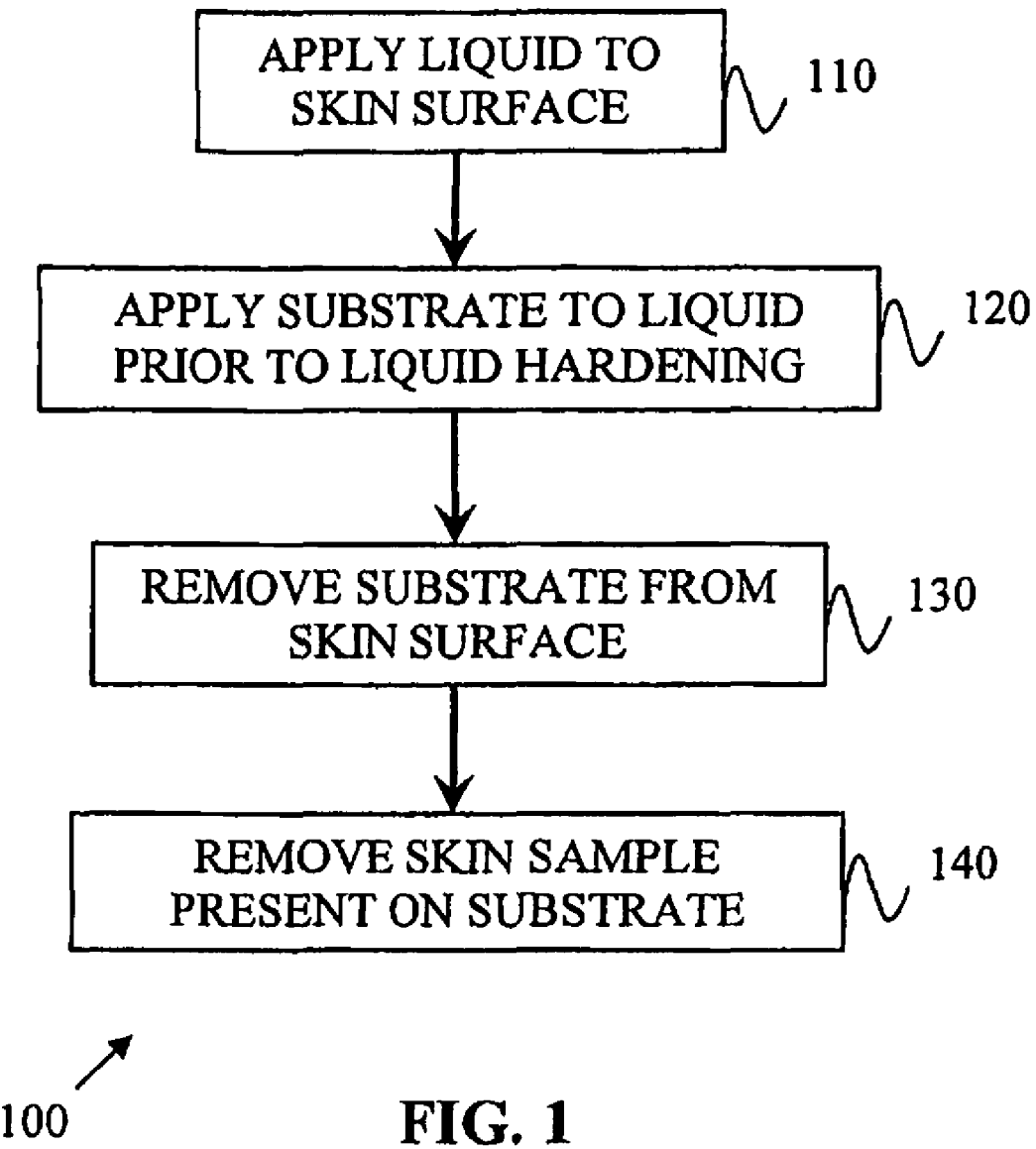
FIG. 1 illustrates a process flow diagram illustrating a method for skin removal using a liquid and a substrate, according to a particular embodiment of the present invention.

FIG. 1 is a process flow diagram illustrating a method 100, in which, at 110, a liquid (which includes a semi-liquid) is applied to a skin surface from which a skin sample is to be extracted. Such a liquid is configured to harden, and prior to hardening, at 120, a substrate is placed within or upon the liquid. With such an arrangement, the liquid hardens and becomes affixed in the hardened state to both the substrate and the skin surface. Thereafter, at 130, the substrate can be removed from the skin surface to result in a skin sample being extracted. This skin sample can be removed, at 140, from the substrate.

Figure 2:
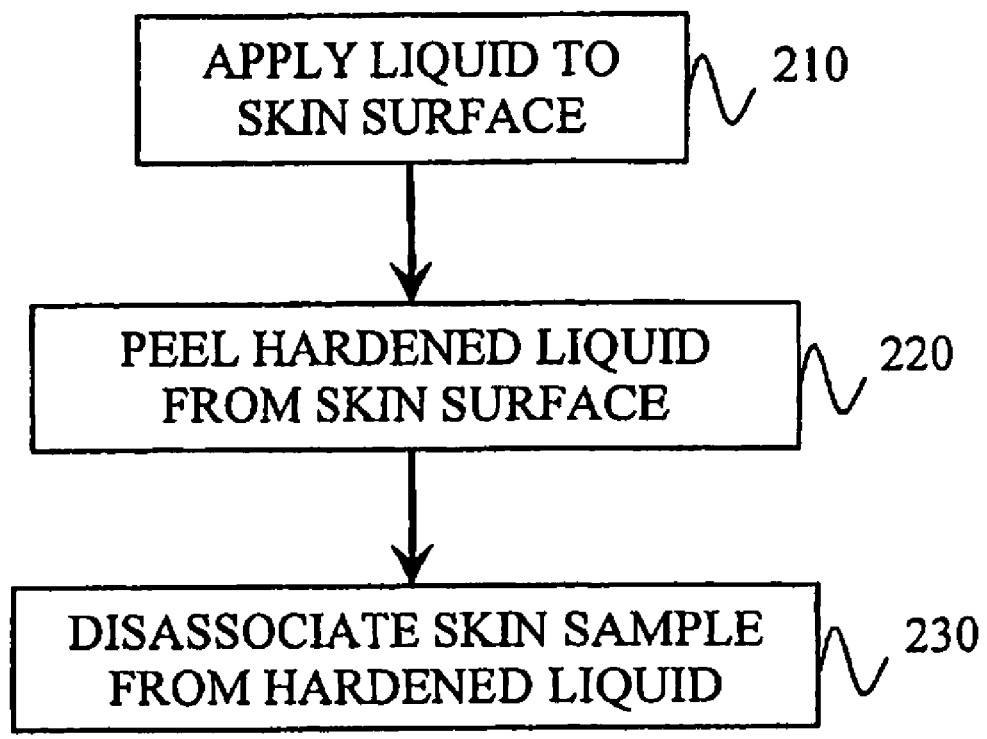
FIG. 2 illustrates a process flow diagram illustrating a method for skin removal using a liquid without a substrate, according to another particular embodiment of the present invention.

FIG. 2 is a process flow diagram illustrating a method 200, in which, at 210, a liquid (which includes a semi-liquid) is applied to a skin surface from which a skin sample is to be extracted. Once the liquid has hardened, at 220, it is peeled away from the skin which results from a skin sample being extracted from the skin surface. Thereafter, at 230, the skin sample can be disassociated from the hardened liquid.

In one embodiment, a liquid or semi-liquid as described herein can be applied to the skin and that once applied to the skin would harden into a hard film or strong gel-like layer. In a particular embodiment, such hardening occurs within five minutes. In another particular embodiment, such hardening takes place in less than one minute.

In another embodiment, the liquid could be applied over a mask that would define the surface area to be sampled and, once hardened, the mask could be lifted off taking the film with it.

In another embodiment, the liquid could simply be applied with a brush or dropper to an area of skin. The area of skin may be normal or lesional. The area of skin may also be on the patient or an in-vitro sample.

In another embodiment, a film is utilized as a substrate. The film would have adhesive-like properties and stick to the skin. These adhesive properties would be sufficient that a layer of skin would remain attached to the film as it is removed from the skin; such as Dermabond and Histoacryl. In a particular embodiment, the film would have sufficient internal strength that it could be removed as a single piece, or at most several pieces (i.e. not too brittle that removal would be a problem) or; a supporting surface (glass slide, metal spatula, plastic film) could be applied to the glue-treated skin whereby a skin sample could be removed as the support was removed.

In another embodiment, the liquid is transformed into a film or gel. This may be done by any method known to one skilled in the art. One exemplary method includes evaporating the solvent when the starting material is liquid by virtue of a solvent, which once evaporated would leave behind the solid film or gel. Another exemplary method includes a reaction with air, such that a chemical reaction with air creates a film or gel. A third exemplary method includes combining two or more ingredients prior to application that will transform into a film or gel once applied to the skin.

In another embodiment the liquid is added to the substrate and the combination applied to the skin and held in place, in the process the liquid conforms to the skin, hardens (polymerizes) thereafter the substrate with the attached stratum corneum is peeled from the skin and the biologic sample harvested as indicated herein.

The methods of collecting RNA from a skin sample could be performed one or more times.

The isolated RNA can further be quantified.

The isolated RNA may further be analyzed to determine the levels of transcription of one or more genes.

Liquids

The liquids of the present invention include any substance capable of forming a bond with skin. A substance which can be applied to the skin as a liquid and that would subsequently transform to a solid (e.g. hard lacquer) or gel as described herein overcomes many of the deficiencies associated with the use of adhesive tape for the recovery of a skin sample. The principle behind the use of applying a liquid to the skin is that liquid can penetrate and fill the natural features of skin that are not accessible to adhesive tape by virtue of its physical properties. By forming a more complete bond with the skin it is likely that a larger sample (as measured by surface area of skin covered) can be removed when the liquid-to-solid agent is removed as compared with tape. This allows for the collection of a skin sample from which RNA can be isolated and analyzed for gene expression.

In one embodiment, the liquid is a sutureless wound closing agent. In a particular embodiment, such agent is a cyanoacrylate-based liquid glue, such as Dermabond or Histoacryl. Liquids of this type have the characteristic in that they are liquids when they are brushed on the skin, but rapidly polymerize to a solid film and form a tight bond with the skin.

In another embodiment, a cyanoacrylate-based liquid glue is applied to the skin and immediately a substrate, such as a glass slide or metal spatula, is applied to the treated area that allows the skin sample to be easily removed. The skin sample is attached to the support base and is subsequently recovered for purification by scraping it off the support with a razor blade.

In a further variation, the use of a substrate can be completely avoided. In order to accomplish this one would have a product like Histoacryl, but which hardens into a strong and flexible film that could be removed by peeling rather than by attachment to a support base. The peeled film could then be added directly to the necessary RNA extraction buffer.

In another embodiment, the liquid is any glue with a low surface tension. Such liquid is capable of molding to the irregular surface of the skin and infiltrating pores, which allows for a strong bond to form between the skin and the liquid. When the liquid is then removed, with or without the use of a substrate, a skin sample containing RNA is easily removed.

Substrates

Any substrate capable of adhering to the liquid may be used in the present invention. Additionally, any substrate capable of acting as a support base for the liquid may be used in the present invention. In one embodiment, the substrate is a glass slide, spatula, cloth or plastic. The skin sample can then be removed from the substrate by scraping or peeling it off.

In another embodiment, a thin plastic strip is directly applied to the glue while it is curing on the skin; this plastic strip would take the place of the glass slide or spatula as a support. The strip can be directly immersed in RNA extraction buffer, i.e. the sample would not have to be removed from the glass slide or spatula. A dispenser of such small plastic films can be provided such that a collection of film strips could be maintained as part of a kit and kept sterile while dispensed on at a time.

Nucleic Acids

As described herein, an aspect of the present disclosure concerns isolated nucleic acids and methods of using these isolated nucleic acids. In certain embodiments, the nucleic acid sequences disclosed herein have utility as hybridization probes or amplification primers. These nucleic acids may be used, for example, in diagnostic evaluation of skin tissue samples. In certain embodiments, these probes and primers consist of oligonucleotide fragments. Such fragments should be of sufficient length to provide specific hybridization to a RNA or DNA tissue sample. The sequences typically will be 10-20 nucleotides, but may be longer. Longer sequences, e.g., 40, 50, 100, 500 and even up to full length, are preferred for certain embodiments.

In one embodiment, probes directed to genes or gene products that are known to be associated with skin disorders are provided. In a particular embodiment, such probes are utilized in RT-PCR. In another particular embodiment, probes are directed to TNF-α, VEGF and/or K17 transcripts are provided.

Nucleic acid molecules having contiguous stretches of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75 80, 85, 90, 95, 100, 125, 150, 175, 200, 250, 300, 400, 500, 600, 750, 1000, 1500, 2000, 2500 or more nucleotides from a sequence selected from the disclosed nucleic acid sequences are contemplated. Molecules that are complementary to the above mentioned sequences and that bind to these sequences under high stringency conditions also are contemplated. These probes will be useful in a variety of hybridization embodiments, such as Southern and Northern blotting.

The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one may desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

The following codon chart may be used, in a site-directed mutagenic scheme, to produce nucleic acids encoding the same or slightly different amino acid sequences of a given nucleic acid:

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In other embodiments, hybridization may be achieved under conditions of, for example, 50 mM Tris-HCl (pH 8.3), 75 mM KCl, 3 mM MgCl$_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional sequence analogs of these sequences. For example, a partial sequence may be used to identify a structurally-related gene or the full length genomic or cDNA clone from which it is derived. Those of skill in the art are well aware of the methods for generating cDNA and genomic libraries which can be used as a target for the above-described probes.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

Amplification of Nucleic Acids

RNA isolated from a skin sample by the methods of the present invention may be used as a template for amplification. It may be isolated from cells contained in the biological sample, according to standard methodologies. For particular applications, it may be desired to convert the RNA to a complementary cDNA. In one embodiment, the RNA is whole cell RNA and is used directly as the template for amplification.

Pairs of primers that selectively hybridize to RNA or complementary cDNA corresponding to specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and patients exhibiting the disease. In this way, it is possible to correlate the amount of marker detected with various clinical states. One may also correlate the results in various regions of a patient, such as lesional and unaffected skin, in patients suffering from a skin disorder.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form.

2. Template Dependent Amplification Methods

A number of template dependent processes are available to amplify the marker sequences present in a given template sample. One of the best known amplification methods is the polymerase chain reaction (referred to as PCR).

A reverse transcriptase PCR amplification procedure may be performed in order to quantify the amount of mRNA amplified. Methods of reverse transcribing RNA into cDNA are well known. Alternative methods for reverse transcription utilize thermostable DNA polymerases. Polymerase chain reaction methodologies are well known in the art.

Another method for amplification is the ligase chain reaction ("LCR"). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs.

Qbeta Replicase may also be used as still another amplification method in the present invention. In this method, a replicative sequence of RNA which has a region complementary to that of a target is added to a sample in the presence of an RNA polymerase. The polymerase will copy the replicative sequence which may then be detected. This method is well known in the art.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention. Such methods are well known in the art.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated. This method is also well known in the art.

Other nucleic acid amplification procedures include transcription-based amplification systems (TAS), including nucleic acid sequence based amplification (NASBA) and 3SR. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

A nucleic acid amplification process involving cyclically synthesizing single-stranded RNA ("ssRNA"), ssDNA, and double-stranded DNA (dsDNA), may also be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Methods based on ligation of two (or more) oligonucleotides in the presence of nucleic acid having the sequence of the resulting "di-oligonucleotide", thereby amplifying the di-oligonucleotide, may also be used in the amplification step of the present invention.

3. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods.

Alternatively, chromatographic techniques may be employed to effect separation. There 565 are many kinds of chromatography which may be used in the present invention: adsorption, partition, ion-exchange and molecular sieve, and many specialized techniques for using them including column, paper, thin-layer and gas chromatography.

4. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

Expression products may also be analyzed by use of a biochip, bioarray or other high-throughput technology. Such technology is well-known to those skilled in the art. Such technologies are also capable of analyzing a variety of gene products at one time. These methods are capable of measuring expression by modification of traditional methods for measuring expression, as described above. For instance, quantification can be done by measuring a phosphor image of a radioactive-labeled probe binding to a spot of a microarray, utilizing a phosphor imager and imaging software.

Genes and Skin Disorders of Interest

The expression of any gene of interest may be determined by the methods of the present invention. In one embodiment, the gene expression of one or more genes associated with skin disorders is analyzed. In another embodiment, the relative levels of housekeeping genes, such as GAPDH, are analyzed. In an additional embodiment, the levels of genes associated with one or more skin disorders are determined. In a particular embodiment, the expression levels of TNF-α, VEGF and K16 are determined. In another particular embodiment, the relative level of one or more housekeeping genes is compared to that of TNF-α, VEGF and/or K16.

The gene expression of any gene associated with a skin disorder may be analyzed by the methods of the present invention. Such analysis may be done as a predictive measure to determine a patient's response to a drug prior to starting administration of the drug. In a particular embodiment, the patient has psoriasis and the drug is enbrel. In a patient with psoriasis, only approximately 50% are responsive to enbrel and, on average, costs of the drug range from $15,000 to $25,000 per year. Hence, it is helpful to know if the patient will be responsive to the drug before or shortly after beginning administration of enbrel.

The analysis of the gene expression of one or more genes may also be done to monitor a patient's response to a particular treatment regime. Such treatment regime may include any treatment associated with a skin disorder.

The methods of the present invention may be used with a patient suffering from or suspected of having any skin disorder. In a particular embodiment, such skin disorders include, but are not limited to, psoriasis, irritant and allergic contact dermatitis, melanoma, and atopic dermatitis.

The expression levels of any gene associated with one or more skin disorders may be analyzed according to the methods of the present invention.

Sample Collection Kit

A kit containing the materials needed to practice the methods of the present invention is also provided. In one embodiment, a liquid, a substrate, cell lysis butter suitable for preservation of RNA, and instructions to collect the RNA sample are provided in a kit.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Collection of RNA from Skin Sample: Histoacryl was painted onto an area of the skin approximately 2 cm×2 cm and the end of a glass microscope slide was pressed directly onto the painted area and held against the skin for 30 seconds; the slide was then slowly removed and was observed to have an adherent skin sample. Using a single edged razor blade the skin sample is scraped from the slide onto a weighing paper and then placed into a 1.5 ml eppendorf tube containing RNA extraction buffer (Buffer RLT, RNeasy Extraction Kit; Qiagen, Valencia, Calif.). The sample was purified according to the manufacturer's directions and eluted from the supplied column in 30 microliters of purified water; the sample was stored at −800 C until assay.

RNA Quantification and Analysis: Purified RNA was then assayed for GAPDH mRNA as follows. RNA samples (including RNA controls) were reverse transcribed using Sensiscript reverse transcriptase (Sensiscript Reverse Transcripase Kit, Qiagen, Valencia, Calif.) as described by the manufacturer using 5 microliter aliquots of purified RNA; samples were reverse transcribed in triplicate and a no-RT control was also included. The resulting solution of cDNA was diluted 5-fold with sterile water and assayed for human glyceraldehyde phosphotransferase (GAPDH) using Real-Time PCR and assay reagents purchased from Applied Biosystems (Taq-Man Gene Expression Assays, GAPDH 4326317E; Applied Biosystems, Foster City, Calif.) as described in Benson et al (2006). The resulting Ct values are shown in Table 1. All no-RT controls did not produce detectable signals. Real-Time PCR and Ct values are discussed in Applied Biosystems user Bulletin No. 2 http://docs.appliedbiosystems.com/pe-biodocs/04303859.pdf Example One In order to test the concept of using a liquid adhesive to recover a superficial skin sample the following experiment was performed. The deltoid region on a male subject was cleansed with an alcohol wipe and Histoacryl was applied to an area approximately 2 cm×2 cm. The end of a glass microscope slide was immediately pressed to the painted skin surface and held for approximately 30 seconds. The slide clearly bonded to the skin during this time and was removed slowly; as the slide was removed a skin sample could be observed adherent to the slide. Once removed, the slide was placed on a level surface and a single edged razor blade was used to scrape the sample off the slide and into a 1.5 ml eppendorf tube. The sample was then extracted for RNA and the RNA assayed by Real-Time PCR (see Materials and Methods). This procedure was repeated at a total of four skin sites.

TABLE 1

Real-time PCR data for RNA Recovered From Skin

| Sample ID[a] | $C_t$ value[b] |
|---|---|
| 1 | 27.92 |
| 1 | 27.57 |
| 2 | 32.39 |
| 2 | 31.9 |
| 2 | 31.66 |
| 3 | 34.76 |
| 3 | 34.73 |
| 3 | 34.68 |
| 4 | 29.98 |
| 4 | 30.32 |
| 4 | 29.88 |
| 1280 pg/ul | 27.16 |
| 1280 pg/ul | 27.41 |
| 320 pg/ul | 29.09 |
| 320 pg/ul | 28.91 |
| 200 pg/ul | 29.58 |
| 200 pg/ul | 29.95 |
| 100 pg/ul | 30.55 |
| 100 pg/ul | 30.77 |

[a]Samples 1-4 were recovered from the deltoid region of a single male subject; samples 1280 pg/ul-100 pg/ul are positive control samples containing known quantities of human spleen total RNA (concentration of sample used for cDNA synthesis indicated in micograms per microliter); full experimental details can be found in Materials and Methods above.
[b]The number of PCR cycles required to reach the threshold signal for GAPDH mRNA detection.

The results of each single application of Histoacryl and removal of sample are shown in Table 1. Each RNA sample was assayed in triplicate and those results are shown in the table along with data for assays of known amounts of human spleen RNA. The results in Table 1 clearly demonstrate that significant quantities of RNA were recovered using the methods of the present invention.

Example Two

Histoacryl is painted onto an area of the skin 1.5 cm×1.5 cm and allowed to dry for up to 5 minutes. Using forceps, an edge of the dried film is grabbed and the film peeled from the skin and immediately placed into RNA extraction buffer (Buffer RLT, Rneasy Extraction Kit; Qiagen, Valencia, Calif.). The sample is then placed at minus 20 degrees centigrade until extraction can be continued. RNA purification is continued according to the manufacturer's directions. Purified RNA is then assayed for specific mRNAs by reverse transcription polymerase chain reaction (RT-PCR) using any of several commercially available kits and instruments (examples). Relative gene expression of specific mRNAs and one or more control mRNAs is assayed in each sample. The relative expression of the specific mRNAs of interest is determined by normalizing the amount of specific mRNA to that of each control mRNA in each sample.

Example Three

Histoacryl is painted onto an area of the skin approximately 1 cm×1 cm and a thin (~2 mil) plastic film approximately 1 cm×1 cm is immediately pressed directly onto the treated skin and held for 30 seconds. The film is then removed and placed into a small dish containing Buffer RLT (RNeasy Extraction Kit; Qiagen, Valencia, Calif.). The sample is then placed at minus 20 degrees centigrade for storage or extraction is continued according to the manufacturer's directions. Purified RNA is then assayed for specific mRNAs by reverse transcription polymerase chain reaction (RT-PCR) using any of several commercially available kits and instruments. Relative gene expression of specific mRNAs and one or more control mRNAs is assayed in each sample. The relative expression of the specific mRNAs of interest is determined by normalizing the amount of specific mRNA to that of each control mRNA in each sample.

All of the COMPOSITIONS, and METHODS disclosed and claimed herein can be made and executed without undue experimentation in light of the present disclosure. While the compositions and methods of this invention have been described in terms of particular embodiments, it will be apparent to those of skill in the art that variations may be applied to the COMPOSITIONS, and METHODS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for isolating RNA molecules from a skin sample comprising:
    (a) applying a liquid to a skin surface;
    (b) applying a substrate to said liquid;
    (c) allowing said liquid to harden;
    (d) removing said substrate;
    (e) removing said skin sample from said hardened liquid; and
    (f) isolating RNA from said skin sample.

2. The method of claim 1, wherein the liquid is a sutureless wound closing agents.

3. The method of claim 1, wherein said substrate is selected from the group consisting of a glass slide, a spatula, a plastic film, cloth and plastic.

4. The method of claim 1, wherein said skin sample is collected from a location on a patient selected from the group consisting of the upper back, mastoid process, hand, foot and deltoid.

5. The method of claim 1, further comprising quantifying said RNA.

6. The method of claim 5, wherein said RNA is quantified for the relative levels of transcripts for GAPDH, TNF-α, VEGF and K16.

7. The method of claim 4, wherein said locations include skin that is lesional and unaffected.

8. The method of claim 5, wherein said quantification is predictive of a patient's response to a drug.

9. The method of claim 8, wherein said patient has psoriasis and the drug is etanercept.

10. A method for isolating RNA molecules from a skin sample comprising:
    (a) applying a liquid to a skin surface;
    (b) allowing said liquid to harden;
    (c) removing said hardened liquid comprising a skin sample from said skin surface;
    (d) removing said skin sample from said hardened liquid; and
    (e) isolating RNA from said skin sample.

11. The method of claim 10, wherein said liquid is a sutureless wound closing agent.

12. The method of claim 10, wherein said skin sample is collected from a location on a patient selected from the group consisting of the upper back, mastoid process, hand, foot and deltoid.

13. The method of claim 10, further comprising quantifying said RNA.

14. The method of claim 13, wherein said RNA is quantified for the relative levels of transcripts for GAPDH, TNFα, VEGF and K16.

15. The method of claim 12, wherein said locations include skin that is lesional and unaffected.

16. The method of claim 13, wherein said quantification is predictive of a patient's response to a drug.

17. The method of claim 16, wherein said patient has psoriasis and the drug is etanercept.

* * * * *